US006969528B1

(12) United States Patent
Majoral et al.

(10) Patent No.: US 6,969,528 B1
(45) Date of Patent: Nov. 29, 2005

(54) PHOSPHORUS-CONTAINING DENDRIMERS AS TRANSFECTION AGENTS

(75) Inventors: Jean-Pierre Majoral, Ramonville (FR); Bernard Meunier, Castanet (FR); Anne-Marie Caminade, Toulouse (FR); Christophe Loup, Toulouse (FR); Maria-Antonietta Zanta-Boussif, Strasbourg (FR)

(73) Assignee: Centre National de La Recherche Scientifique-CNRS, Paris (FR)

( * ) Notice: Subject to any disclaimer, the term of this patent is extended or adjusted under 35 U.S.C. 154(b) by 315 days.

(21) Appl. No.: 10/130,739

(22) PCT Filed: Nov. 23, 2000

(86) PCT No.: PCT/FR00/03261

§ 371 (c)(1),
(2), (4) Date: Jul. 2, 2002

(87) PCT Pub. No.: WO01/38335

PCT Pub. Date: May 31, 2001

(30) Foreign Application Priority Data

Nov. 25, 1999 (FR) .................................. 99 14864

(51) Int. Cl.$^7$ .......................... A61K 9/00; A61K 31/74; A61K 47/30; C07F 9/02; C07C 209/06
(52) U.S. Cl. ................... 424/486; 424/400; 424/78.17; 514/772.1; 514/44; 564/12; 564/284; 564/386
(58) Field of Search ........................ 435/455; 564/386, 564/248, 12

(56) References Cited

U.S. PATENT DOCUMENTS 6,440,405 B1 * 8/2002 Cooper et al. ........... 424/78.17

FOREIGN PATENT DOCUMENTS

WO    WO 95 02397 A    1/1995

OTHER PUBLICATIONS

Launay et al. Synthesis of bowl-shpaed dendrimers from generation 1 to generation 8. Journal of Organometallic Chemistry, vol. 529, pp. 51-58, 1997.*
Prevote et al. Phosphate-, phosphite-, Ylide-, and phosphonate-terminated dendrimers. Journal of Organic Chemistry, vol. 62, pp. 4834-4841, 1997.*
C. Galliot; "Regioselective Stepwise Growth Of Dendrimer Units In The Internal Voids Of A Main Dendrimer"; Sep. 26, 1997; pp. 1981-1984; vol. 277; SCIENCE; Lancaster, PA.
C. Larre; "Phosphorus-Containing Dendrimers: Chemoselective Functionalization of Internal Layers"; Apr. 29, 1998; pp. 4029-4030; vol. 120, No. 16; American Chemical Society; Washington, D.C.
D. Prevote; "Phosphate-, Phosphite-, Ylide-, and Phosphonate-Terminated Dendrimers"; Jul. 11, 1997; pp. 4823-4841; vol. 62, No. 14; Journal of Organic Chemistry.
C. Loup; "Preparation of Water-Soluble Cationic Phosphorus-Containing Dendrimers as DNA Transfecting Atents"; Dec. 1999; pp. 3644-3650; vol. 5, No. 12; VCH Publishers.
V. Maraval; "Rapid Synthesis of Phosphorus-Containing Dendrimers with Controlled Molecular Architectures: First Example of Surface-Block, Layer-Block, and Segment-Block Dendrimers Issued from the Same Dendron"; Mar. 22, 2000; pp. 2499-2511; vol. 122, No. 11; Journal of the American Chemical Society.

* cited by examiner

Primary Examiner—Terry McKelvey
Assistant Examiner—Jennifer Dunston
(74) Attorney, Agent, or Firm—Alston & Bird LLP (57) ABSTRACT

The invention concerns phosphorus-containing dendrimers and their uses, as gene transfection agents, in vitro and in vivo, including in the treatment of human and animal diseases. These agents or vectors are in particular suited for delivering to appropriate target cells, nucleic acid sequences of interest.

9 Claims, 5 Drawing Sheets

PHOSPHORUS-CONTAINING DENDRIMERS AS TRANSFECTION AGENTS

The present invention relates to phosphorus-containing dendrimers and to uses thereof, as agents for transfecting genes, in vitro and in vivo, including the treatment of human and animal diseases. Said agents or vectors are in particular suitable for delivering nucleic acid sequences of interest to appropriate target cells.

Gene therapy is based on the therapeutic administration of nucleic acids; it requires the use of efficient and safe vectors for the transfer of therapeutic genes and the success thereof therefore depends on the efficiency of gene transfer into the desired cells.

Many compositions capable of transfecting eukaryotic cells with a selective genetic material have already been described and essentially belong to two major types of transfection vectors:
  viral transfection vectors, which are efficient but which have limits for use: not tissue specific, necessity of obtaining constructs for each gene of interest, potential risks for the environment which lead to the setting up of expensive and restrictive clinical infrastructures for the patient and the personnel, and problems of immune response, of production of viral particles by homologous recombination and of potential oncogenic effects;
  nonviral agents (synthetic vectors), capable of promoting the transfer and expression of chemical substances, such as DNA, in eukaryotic cells.

These synthetic vectors must essentially have two functions: condense the DNA to be transfected and promote the cellular attachment thereof and also the passage thereof across the plasma membrane and, optionally, the nuclear membranes; in order to be efficient, such vectors must therefore mimic the function of viruses. However, it appears that the various vectors provided in the prior art do not exhibit these two functions optimally and may also, depending on the cases, be toxic for the cells.

Among these nonviral vectors, mention may be made in particular of preparations of cation lipids, which are particularly cytotoxic (15–18), techniques for encapsulating DNA in liposomes (9–11) and polycationic polymers, such as poly(L-lysine), protamine, polyethyleneimine (12) or cationic dendrimers (polyamidoamines) (13, 14, 27), which associate with the DNA via multiple electrostatic interactions engendering a process of cooperativity, which produces particles called polyplexes, each one giving variable transfection efficiencies depending on their structure and the cell type (25).

More precisely, dendrimers of the polyamidoamine (PAMAM) type are polymers with a spherical and branched structure; they are soluble in aqueous solution and have a layer of primary amines at their surface; they are isomolecular and highly charged at their surface. The various dendrimers described have various types of core: ammonium or ethylenediamine (EDA), from which the polymerization process is initiated. These PAMAM dendrimers contain a defined number of amino groups at the surface of the polymer, which are positively charged at physiological pH. It has been shown that such molecules interact with anions such as nucleic acids and that the DNA/dendrimer complexes are capable of transfecting cells in a way similar to that observed with DNA/polylysine complexes, but with greater efficiency, linked to their solubility and to their structure. In particular, $G_3$–$G_5$ PAMAM dendrimers, comprising, as the core, either $NH_3$ groups or EDA groups, are capable of forming stable complexes with DNA under physiological conditions, and $G_5$–$G_{10}$ dendrimers are capable of transfecting genes. The fact that the capacity of transfection is limited to this group of dendrimers is doubtless linked to the number of amino groups present at their surface and to their spherical shape. The efficiency of the latter depends on the chemical modifications to the initial dendrimeric structure by heat treatment which results in a population of heterodispersed compounds (15, 21).

Over about ten years, research on the chemistry of dendrimers has developed considerably, due to their structure (ordered polyfunctional polymers) and to their particular properties linked to the presence of a considerable number of functionalities at their ends, which provide a large number of surfaces and interfaces, and to the presence of empty zones which allow encapsulation of diverse molecules; this research has led to the synthesis of other structures corresponding to phosphorus-containing dendrimers, such as those described by C. Galliot et al. (18), by C. Larré et al. (19) or by D. Prévôté et al. (28).

However, it emerges from the literature that these phosphorus-containing dendrimers, which are not water-soluble, cannot be used as transfection agents.

In the context of their research, the inventors have now shown that novel phosphorus-containing dendrimers which are functionalized at the level of the inner layers and which comprise protonated tertiary amines as ends, have particularly advantageous properties as vectors for transferring nucleic acids.

A subject of the present invention is polycationic phosphorus-containing dendrimers, characterized in that they consist:
  of a central layer in the form of a core $P_0$ comprising 2 to 8 functionalized groups and, in particular, the group of general formula Ia (also named $N_3P_3$):

(Ia)

or the group of general formula Ib:

of n intermediate layers, which may be identical or different, each one of said intermediate layers consisting of units P1 corresponding to formula II:

(II)

in which:
L is an oxygen, phosphorus or sulfur atom,
M represents one of the following groups:
  an aromatic group di-, tri- or tetra-substituted with alkyl groups, alkoxy groups or unsaturated groups of the $C_1$–$C_{12}$ olefinic, azoic or acetylenic type, all these groups possibly incorporating phosphorus, oxygen, nitrogen, sulfur or halogen atoms, or an alkyl or alkoxy group comprising several substituents as defined when M is an aromatic group, $R_1$ and $R_2$, which may be identical or different, represent a hydrogen atom or one of the following groups: alkyl, alkoxy, aryl, possibly comprising phosphorus, oxygen, sulfur, nitrogen or halogen atoms, with $R_2$ most commonly being different from $R_1$, n is an integer between 1 and 11, E is an oxygen, sulfur or nitrogen atom, said nitrogen atom possibly being linked to an alkyl, alkoxy or aryl group, all these groups possibly incorporating phosphorus, oxygen, nitrogen, sulfur or halogen atoms, an outer layer consisting of units P2, which may be identical or different, corresponding to formula III:

(III)

in which:

$R_5$ represents a hydrogen atom or one of the following groups: alkyl, alkoxy, aryl, these groups possibly comprising phosphorus, oxygen, nitrogen, sulfur or halogen atoms,

W represents one of the following groups: alkyl, alkoxy, aryl, all these groups possibly comprising phosphorus, oxygen, nitrogen, sulfur or halogen atoms, $R_3$ and $R_4$, which may be identical or different, represent a $C_1$–$C_5$ alkyl group,

X represents a hydrogen atom or a $C_1$–$C_5$ alkyl group or is absent, and Z represents a halide ion, an alkylCOO$^-$ group or any other anionic group comprising carbon, oxygen, sulfur, nitrogen, phosphorus or halogen atoms, or is absent.

A preferred group of formula II is in particular the following group:

a preferred group of formula III is in particular the following group:

in which p=1 to 5

Figure 1:
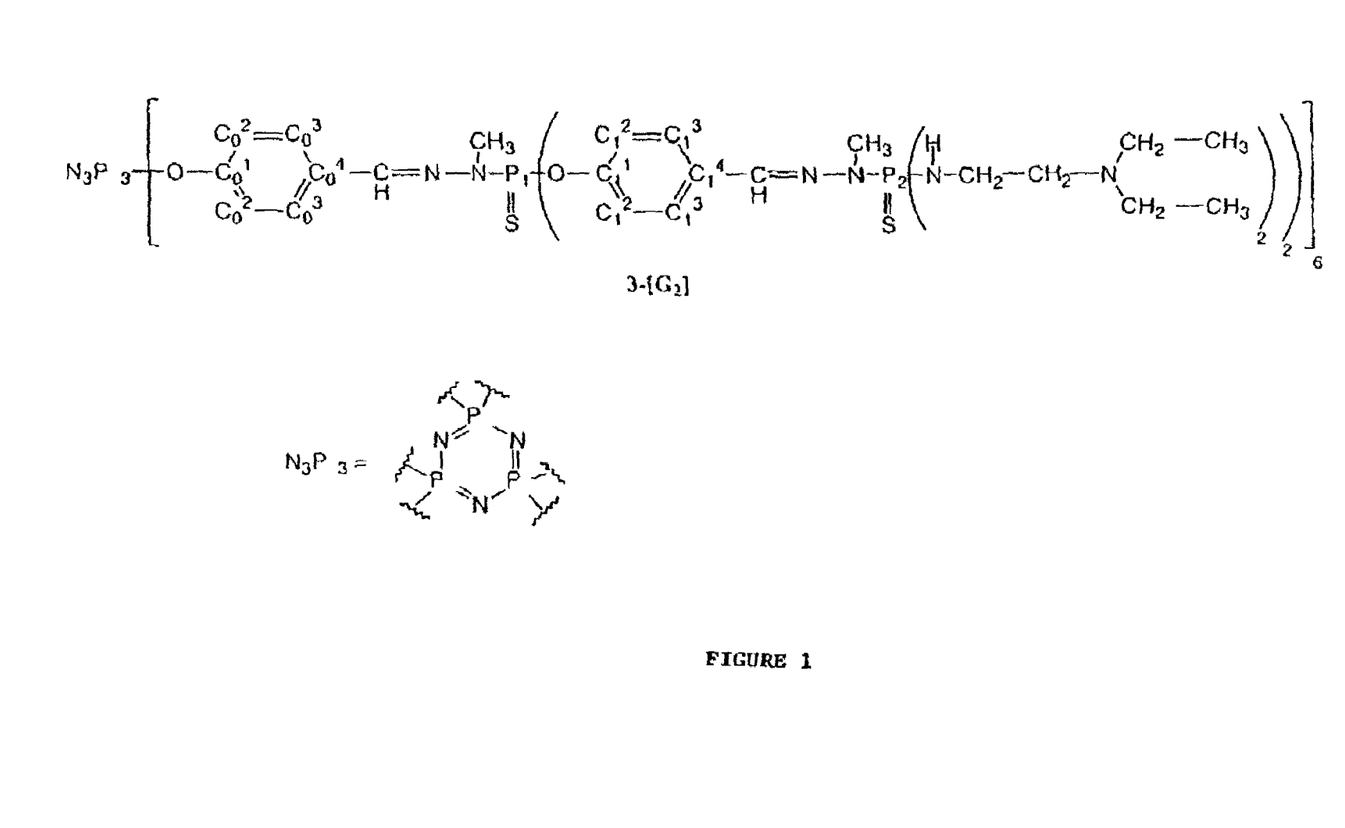
FIG. 1 illustrates the structure of the central core $P_0$ ($N_3P_3$) and the dendrimer according to the invention of the 3-[$G_2$] type.
Figure 2:
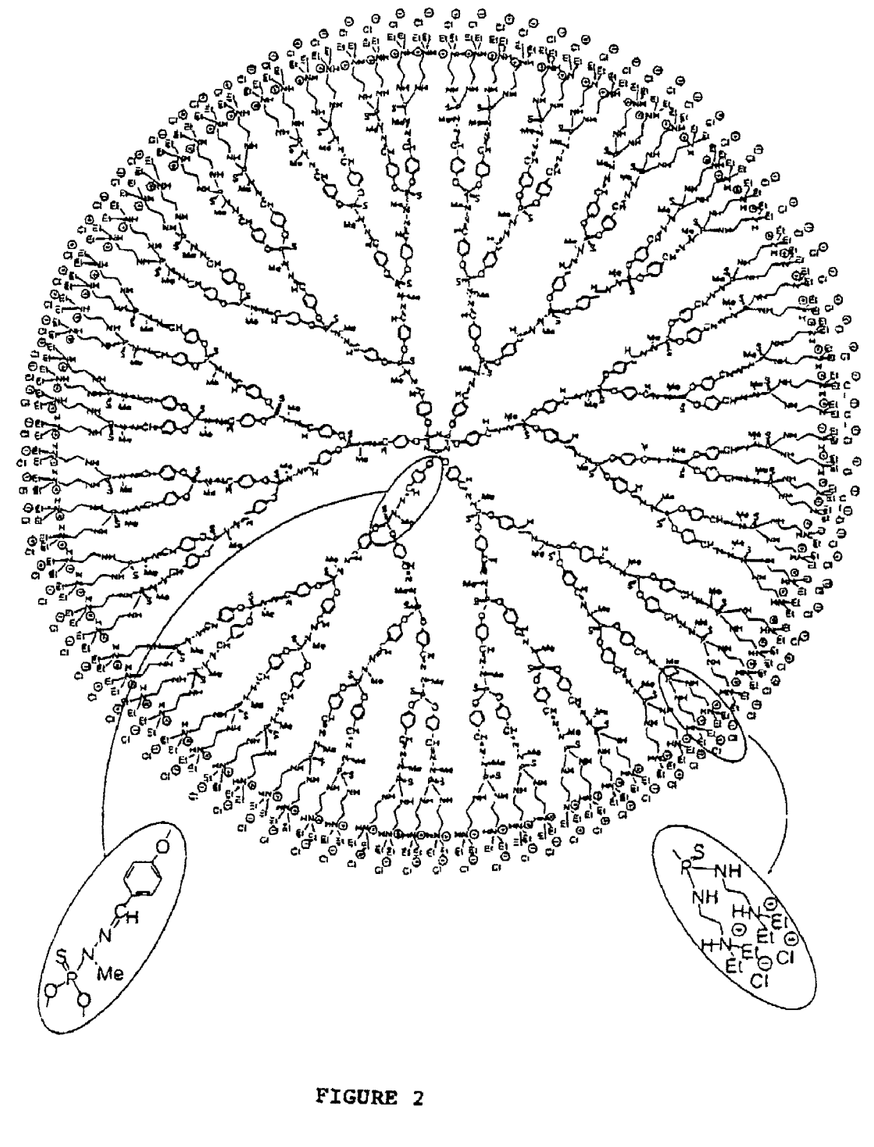
FIG. 2 illustrates a dendrimer according to the invention of the 2-[$G_4$] type.
Figure 3:
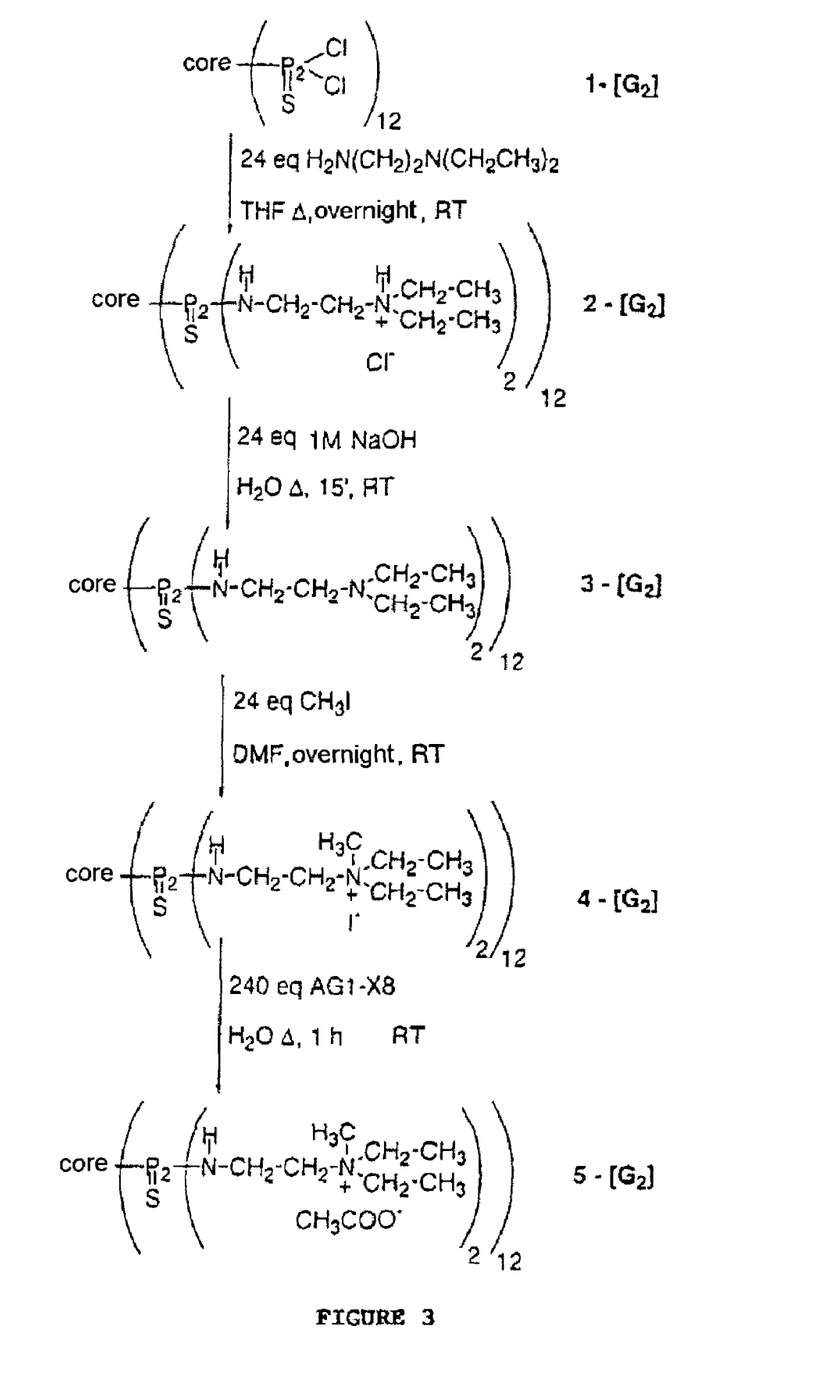
FIG. 3 illustrates a method for preparing the dendrimers according to the invention.

Such compounds represent dendrimers and are in particular represented in FIGS. 1 to 3.

The expression "alkoxy" denotes the radicals of general formula R'O—, for example methoxy, ethoxy, propoxy, isopropoxy, butoxy, isobutoxy, tert-butoxy groups.

The expression "alkyl" denotes the linear- or branched-chain radicals containing up to 8 carbon atoms. Among these radicals, mention may be made of methyl, ethyl, propyl, isopropyl, butyl, isobutyl, sec-butyl, tert-butyl, pentyl, hexyl, heptyl or octyl radicals.

The expression "aryl" denotes, for example, a phenyl radical optionally substituted with one or more alkoyl or alkoxyl radicals or with a chlorine, bromine or fluorine atom, or a 5- or 6-membered aromatic heterocyclic radical containing 1 to 2 hetero atoms such as nitrogen or oxygen. Among these aryl radicals, mention may be made of (o-, m-, or p-)phenyl, (3,4-, 2,6-, 2,3-)methoxyphenyl, (o-, m-, or p-)dimethoxyphenyl, tolyl, thienyl or pyridyl radicals.

It is possible to obtain several types of product designated, in general, by the formula A—[$G_n$], in which A defines the type of terminal unit and $G_n$ defines the number of layers of intermediate units P1 (corresponding to the number of generations):

the series of compounds 2-[$G_n$] has terminal units of the said formula III, in which X represents a hydrogen atom, p is equal to 2, $R_3$ and $R_4$ are identical and represent ethyl groups, Z is a chloride ion and n is an integer between 1 and 11, preferably between 1 and 10 (see FIG. 3);

the series of compounds 3-[$G_n$] has terminal units of formula III, in which X is empty, p is equal to 2, $R_3$ and $R_4$ are identical and represent ethyl groups, Z is empty and n is an integer between 1 and 11, preferably between 1 and 10 (see FIG. 3);

the series of compounds 4-[$G_n$] has terminal units of formula III, in which X represents a methyl group, p is equal to 2, $R_3$ and $R_4$ are identical and represent ethyl groups, Z is an iodide ion and n is an integer between 1 and 11, preferably between 1 and 10 (see FIG. 3);

the series of compounds 5-[$G_n$] has terminal units of formula III, in which X represents a methyl group, p is equal to 2, $R_3$ and $R_4$ are identical and represent ethyl groups, Z is a group $CH_3COO^-$ and n is an integer between 1 and 11, preferably between 1 and 10 (see FIG. 3);

the series of compounds 1-[$G_n$] has $Cl_2$ terminal units and n is an integer between 1 and 11, preferably between 1 and 10 (see FIG. 3) (intermediate products for the preparation of the dendrimers according to the invention).

The polycationic phosphorus-containing dendrimers according to the invention have a certain number of advantages compared to the dendrimers of the prior art used as gene vectors:

they are isomolecular and, as a result, are reproducible (high degree of purity), they are charged, which confers on them a particular affinity with respect to the nucleic acids to be transferred and therefore good transporter quality, they can be functionalized both at the surface and in the inner layers, they are water-soluble without degradation within a large pH range (3 to 12) (stability in aqueous solution for several months). This represents a clear advantage compared with the dendrimers of the PAMAM type which must be heat-degraded (relatively poorly reproducible step) to give compounds which are active in transfection, they are relatively noncytotoxic (viability of transfected cells greater than 80%).

The phosphorus-containing dendrimers according to the invention may be obtained, in a reproducible manner, by controlled growth of the dendrimeric structure by addition of successive layers of motifs or units $H_2N—N(R_2)—P(S)Cl_2$ of formula VIII (example of product of formula II). The central core or block of formula VII (see FIGS. 1 and 2) correspond to a hexachlorocyclotriphosphazene unit ($Cl_6N_3P_3$) modified by the triethylammonium of 4-hydroxybenzaldehyde. This core, which comprises 6 terminal aldehyde functions, is brought into contact with a dichlorophosphonoalkylhydrazide of formula VIII $H_2N—N(Alk)-P(S)Cl_2$ to produce a dendron comprising dichlorothiophosphine, $P(S)Cl_2$, terminal units, which can be brought into contact once more with a 4-hydroxybenzaldehyde salt of formula VI, to produce, by iteration, each dendrimer generation. The 1st, 2nd, 3rd, 4th and 5th dendrimer generations comprise, respectively, 6, 12, 24, 48 and 96 $Cl_2$ terminal units, which can be treated with N,N-dialkylethylenediamine, to produce cationic dendrimers after protonation: 2-[$G_1$] to 2-[$G_5$], in accordance with FIG. 3.

The polycationic phosphorus-containing dendrimers have 12, 24, 48, 96 or 192 peripheral positive charges, respectively, for the 1st, 2nd, 3rd, 4th and 5th dendrimer generations.

The methylated forms (5-[$G_1$] to 5-[$G_5$]) are prepared from the corresponding neutral terminal amines (3-[$G_1$] to 3-[$G_5$]) by methylation in the presence of methyl iodide, followed by an iodide/acetate exchange using a suitable resin (see example 1).

The purity and integrity of the dendrimers is verified by spectral analysis ($^1H$, $^{13}C$ and $^{31}P$ NMR).

Only 8 to 10% of the terminal branches of the methylated dendrimers (5-[$G_1$] to 5-[$G_5$]) exhibit a deficit in methyl groups.

More precisely, the dendrimers according to the invention may be prepared in the following way:

(1) reaction of a product of formula V (also named $N_3P_3$)

(V)

in which $R_1$ represents a group comprising an aldehyde function of formula VI:

(VI)

so as to obtain a product of formula VII: $N_3P_3$ $(OC_6H_4CHO)_6$ comprising 6 aldehyde functions (central layer consisting of a core $P_0$; FIG. 3), (2) reaction of the product of formula VII obtained in (1) with a dichlorophosphonohydrazide of formula VIII: $H_2N—N(R_2)—P(S)Cl_2$ to produce a dendron of the 1-[$G_n$] type comprises $Cl_2$ terminal units, (3) reiteration of steps (1) and (2) on the product obtained in (2) to produce a number n of intermediate layers; the 1st, 2nd, 3rd, 4th and 5th dendrimer generations comprise, respectively, 6, 12, 24, 48 and 96 $Cl_2$ terminal units, and (4) treatment of said $Cl_2$ terminal units with N,N-dialkylethylenediamine, to produce cationic dendrimers according to the invention after protonation.

A subject of the present invention is also a composition capable of acting as an agent for transfecting a nucleic acid sequence into a eukaryotic cell, characterized in that it comprises a nucleic acid and a polycationic phosphorus-containing dendrimer as defined above, coupled to said nucleic acid.

According to an advantageous embodiment of said composition, it also comprises at least one pharmaceutically acceptable vehicle.

According to another advantageous embodiment of said composition, the N/P ratio, in which N corresponds to the terminal cationic groups of the dendrimer (charged amines) and P corresponds to the phosphate groups of said nucleic acid, is between 5 and 10.

According to another advantageous embodiment of said composition, it also comprises an agent for permeabilizing the membrane, capable of transporting said nucleic acid across the cytoplasmic or endosomal membranes of said eukaryotic cell.

According to yet another advantageous embodiment of said composition, said polycationic phosphorus-containing dendrimer is associated noncovalently with said nucleic acid.

Advantageously, the polycationic phosphorus-containing dendrimers according to the invention, selected in the series 2-[$G_n$] in which n=3–5, are particularly advantageous as vectors for transferring nucleic acid, while the dendrimers of the series 5-[$G_n$] are toxic and relatively inefficient in transfecting nucleic acids into eukaryotic cells, both in the presence and absence of serum.

This phenomenon is perhaps linked to a high density of stable positive charges, which may cause rupturing of the cell membrane and thus lead to cell death. It is not possible to decrease the charge density for the alkylated products without degrading the dendrimers, whereas the charge density of the series 2-[$G_n$] may be modulated by microenvironmental modifications of the pH at the level of the cell membrane. In addition, the possibility of modulating the charge density of this series of dendrimers may constitute a key factor in the release of the gene transported in the endosomes. These dendrimers thus perhaps act as a proton reservoir in the cellullar compartments, their charge density being controlled by ATPase-dependent proton pumps and by modifications of the intracellular chloride concentration. The possibility of decreasing the cationic charge density of these dendrimers outside and inside the cells should be favorable to their use in vivo.

Besides the arrangements above, the invention also comprises other arrangements, which will emerge from the following description, which refers to examples of implementation of the method which is the subject of the present invention, and also to the attached drawings in which.

It should be clearly understood, however, that these examples are given only by way of illustration of the subject of the invention, in which they in no way constitute a limitation.

EXAMPLE 1

Preparation of the Dendrimers According to the Invention

General Methods and Products Used

All the manipulations were carried out using common techniques under conditions of a strong vacuum or under argon. The $^1$H, $^{31}$P and $^{13}$C NMR spectra were recorded on Brucker spectrometers (AC80, AC200 and AC250). The $^{31}$P NMR chemical shifts of the reagents are expressed in ppm relative to 85% of $H_3PO_4$. The numbering used for the NMR is detailed on FIG. 1. The 1-[$G_n$] dendrimers were synthesized according to published protocols (16, 17). In the abbreviation 1-[$G_n$], the number 1 corresponds to a dendrimer with ends C1, 2, 3, 4 or 5 for ends —$NH(Et)_2{}^+Cl^-$, —$N(Et)_2$, —$NMe(Et)_2{}^+I^-$ or —$NMe(Et)_2{}^+OAc^-$, respectively, and n corresponds to the number of generations of the dendrimer (number of intermediate layers). The methyl iodide and the N,N-diethylethylenediamine were supplied by Aldrich and the AG1-X8 resin, which has a high capacity for anion exchange, was supplied by Biorad.

General Procedures for Synthesizing the Products of the 2-[$G_n$] Type

N,N-Diethylethylenediamine (n=1, 93 μl, 0.66 mmol; n=2, 71 μl, 0.5 mmol; n=3, 68 μl, 0.48 mmol; n=4, 61 μl, 0.43 mmol; n=5, 60 μl, 0.42 mmol) was added dropwise, using a syringe, to a solution containing 100 mg of dendrimer 1-[$G_n$] (n=1, 55 μmol; n=2, 21 μmol; n=3, 10 μmol; n=4, 4.5 μmol; n=5, 2.2 μmol) in 15 ml of distilled THF (THFΔ), with vigorous stirring. After stirring overnight at room temperature (RT), the solvent was removed by filtration. The white powder obtained was washed twice with 20 ml of distilled THF and dried by evaporation. The protons produced during the coupling reaction were captured by the terminal tertiary amine residues and, consequently, the 2-[$G_n$] dendrimers were obtained in the form of chlorides.

The first generation of dendrimer 2-[$G_1$] is obtained with a yield of 80%. The NMR data are as follows:

$^{31}$P {$^1$H} NMR ($CD_3OD$): δ=7.9 ($P_0$), 69.6 ($P_1$).

$^1$H NMR ($d_6$-DMSO): δ=1.3 (t, $^3J_{HH}$=6.3 Hz, 72H, $CH_2CH_3$), 3.0–3.5 (m, 114H, $CH_3$—N—$P_1$, $CH_2$), 5.7 (br m, 12H, N—H), 7.1 (d, $^3J_{HH}$=8.4 Hz, 12H, $C_0{}^2$—H), 7.9 (s, 6H, CH=N), 7.9, (d, $^3J_{HH}$=8.4 Hz, 12H, $C_0{}^3$—H), 10.8 (br s, 12H, $^+$N—H).

$^{13}$C {$^1$H} NMR ($CD_3OD$): δ=9.7 (s, $CH_2CH_3$), 33.3 (d, $^2J_{CP1}$= 10.3 Hz, $CH_3$—N—$P_1$), 37.9 (s, $CH_2$—N—$P_1$), 49.5 (s, $CH_2CH_3$), 53.9 (d, $^3J_{CP1}$=6.2 HZ, $CH_2$—$CH_2$—N—$P_1$) 122.6 (s, $C_0{}^2$), 129.8 (s, $C_0{}^3$), 135.0 (s, $C_0{}^4$), 139.3 (d, $^3J_{CP1}$=11.6 Hz, CH=N), 152.4 (d, $^2J_{CP0}$=7.3 Hz, $C_0{}^1$).

UV-vis ($H_2O$): $\lambda_{max}$($\epsilon$, $M^{-1}\times cm^{-1}$) 284 nm (1.2×10$^5$).

Second generation of dendrimer 2-[$G_2$] (yield= 95%):

$^{31}$P {$^1$H} NMR ($CD_3OD$): δ=8.5 ($P_0$), 62.0 ($P_1$), 69.6 ($P_2$).

$^1$H NMR ($d_6$-DMSO): δ=1.3 (br s, 144H, $CH_2CH_3$), 3.0–3.6 (br m, 246H, $CH_3$—N—$P_{1,2}$, $CH_2$), 5.6 (br m, 24H, N—H), 7.0–7.4 (br m, 36H, $C_0{}^2$—H, $C_1{}^1$—H), 7.7–8.2 (m, 54H, CH=N, $C_0{}^3$—H, $C_1{}^3$—H), 10.7 (br s, 24H, $^+$N—H).

$^{13}$C {$^1$H} NMR ($CD_3OD$): δ=9.6 (s, $CH_2CH_3$), 33.0 (d, $^2J_{CP2}$= 10.6 Hz, $CH_3$—N—$P_2$), 34.2 (d, $^2J_{CP1}$=11.8 Hz, $CH_3$—N—$P_1$), 37.8 (s, $CH_2$—N—$P_2$), 49.2 (s, $CH_2CH_3$), 53.9 (d, $^3J_{CP2}$= 6.3 Hz, $CH_2$—$CH_2$—N—$P_2$), 122.8 (s, $C_0{}^2$), 123.0 (d, $^3J_{CP1}$= 3.0 Hz, $C_1{}^2$), 129.7 (s, $C_1{}^3$), 130.0 (S, $C_0{}^3$), 134.3 (s, $C_0{}^4$), 135.0 (s, $C_1{}^4$), 139.1 (d, $^3J_{CP2}$=12.5 Hz, CH=N), 141.3 (d, $^3J_{CP1}$=15.4 Hz, CH=N), 152.6 (d, $^2J_{CP1}$= 7.3 Hz, $C_1{}^1$), 152.6 (s, $C_0{}^1$).

UV-vis ($H_2O$): $\lambda_{max}$($\epsilon$, $M^{-1}\times cm^{-1}$) 284 nm (3.1×10$^5$).

Third generation of dendrimer 2-[$G_3$] (yield= 95%):

$^{31}$P {$^1$H} NMR ($CD_3OD$): δ=8.6 ($P_0$), 61.5 ($P_1$), 62.3 ($P_2$), 69.5 ($P_3$).

$^1$HNMR ($d_6$-DMSO): δ=1.3 (br s, 288H, $CH_2CH_3$), 3.0–3.5 (br m, 510H, $CH_3$—N—$P_{1,2,3}$, $CH_2$), 5.7 (br s, 48H, N—H), 7.0–7.5 (br m, 84H, $C_0{}^2$—H, $C_1{}^2$—H, $C_2{}^2$—H), 7.7–8.2 (br m, 126H, CH=N, $C_0{}^3$—H, $C_1{}^3$—H, $C_2{}^3$—H), 10.8 (br s, 48H, $^+$N—H).

$^{13}$C {$^1$H} NMR ($CD_3OD$): δ=9.6 (s, $CH_2CH_3$), 33.1 (d, $J_{CP3}$= 9.4 Hz, $CH_3$—N—$P_3$), 34.2 (m, $CH_3$—N—$P_{1,2}$), 37.6 (s, $CH_2$—N—$P_3$), 49.2 (s, $CH_2CH_3$), 53.7 (d, $^3J_{CP3}$=6.3 Hz, $CH_2$—$CH_2$—N—$P_3$), 123.2 (br s, $C_0{}^2$, $C_1{}^2$, $C_2{}^2$), 129.6 (br s, $C_0{}^3$, $C_1{}^3$, $C_2{}^3$), 134.0 (s, $C_0{}^4$, $C_1{}^4$), 134.8 (s, $C_2{}^4$), 139.0 (br s, $C_2$—CH=N), 141.4 (br s, CH=N), 152.4 (d, $J_{CP2}$=7.3 Hz, $C_2{}^1$), 152.8 (br s, $C_0{}^1$, $C_1{}^1$).

UV-vis ($H_2O$): $\lambda_{max}$($\epsilon$, $M^{-1}\times cm^{-1}$) 286 nm (7.3×10$^5$).

Fourth generation of dendrimer 2-[$G_4$] (yield= 95%):

$^{31}$P {$^1$H} NMR ($CD_3OD$): δ=8.4 ($P_0$), 62.0 ($P_{1,2,3}$), 69.4 ($P_4$).

$^1$H NMR ($d_6$-DMSO): δ=1.3 (br s, 576H, $CH_2CH_3$), 3.0–3.5 (m, 1038H, $CH_3$—N—$P_{1,2,3,4}$, $CH_2$), 5.6 (br s, 96H, N—H), 7.0–7.5 (br m, 180H, $C_0{}^2$—H, $C_1{}^2$—H, $C_2{}^2$—H, $C_3{}^2$—H), 7.7–8.2 (m, 270H, CH=N, $C_0{}^3$—H, $C_1{}^3$—H, $C_2{}^3$—H, $C_3{}^3$—H), 10.8 (br s, 96H, $^+$N—H).

$^{13}$C {$^1$H} NMR ($CD_3OD$): δ=9.7 (s, $CH_2CH_3$), 33.2 (d, $^2J_{CP4}$= 9.2 Hz, $CH_3$—N—$P_4$), 34.3 (d, $^2J_{CP}$=10.1 Hz, $CH_3$—N—$P_{1,2,3}$), 37.7 (s, $CH_2$—N—$P_4$), 49.2 (s, $CH_2CH_3$), 53.8 (d, $^3J_{CP4}$= 5.5 Hz, $CH_2$—$CH_2$—N—$P_4$), 123.1 (br s, $C_0{}^2$, $C_1{}^2$, $C_2{}^2$, $C_3{}^2$) 129.7 (br s, $C_0{}^3$, $C_1{}^3$, $C_2{}^3$, $C_3{}^3$), 134.2 (s, $C_0{}^4$, $C_1{}^4$, $C_2{}^4$), 134.9 (s, $C_3{}^4$), 139.2 (br s, $C_3{}^4$—CH=N), 141.5 (br s, CH=N), 152.5 (d, $^3J_{CP3}$=7.4 Hz, $C_3{}^1$), 153.0 (br s, $C_0{}^1$, $C_1{}^1$, $C_2{}^1$).

UV-vis ($H_2O$): $\lambda_{max}$ ($\epsilon$, $M^{-1}\times cm^{-1}$) 288 nm (1.7×10$^6$).

Fifth generation of dendrimer 2-[$G_5$] (yield= 95%):

$^{31}$P {$^1$H} NMR ($CD_3OD$): δ=62.0 ($P_{1,2,3,4}$), 69.3 ($P_5$).

$^1$H NMR ($d_6$-DMSO): δ=1.3 (br s, 1152H, $CH_2CH_3$), 2.9–3.5 (br m, 2094H, $CH_3$—N—$P_{1,2,3,4,5}$, $CH_2$), 5.6 (br s, 192H, N—H), 7.0–7.5 (m, 372H, $C_0{}^2$—H, $C1^2$—H, $C_2{}^2$—H, $C_3{}^2$—H, $C_4{}^2$—H), 7.7–8.2 (m, 558H, CH=N, $C_0{}^3$—H, $C_1{}^3$—H, $C_2{}^3$—H, $C_3{}^3$—H, $C_4{}^3$—H), 10.8 (br s, 192H, N—H).

$^{13}$C {$^1$H} NMR ($CD_3OD$): δ=9.7 (s, $CH_2CH_3$), 33.2 (br s, $CH_3$—N—$P_5$), 34.3 (br s, $CH_3$—N—$P_{1,2,3,4}$), 37.8 (s, $CH_2$—N—$P_5$), 49.2 (s, $CH_2CH_3$), 53.8 (s, $CH_2$—$CH_2$—N—$P_5$), 123.1 (br s, $C_0{}^2$, $C_1{}^2$, $C_2{}^2$, $C_3{}^2$, $C_4{}^2$), 129.7 (br s, $C_0{}^3$, $C_1{}^3$, $C_2{}^3$, $C_3{}^3$, $C_4{}^3$), 134.2 (s, $C_0{}^4$, $C_1{}^4$, $C_2{}^4$, $C_3{}^4$), 134.9 (s, $C_4{}^4$), 139.2 (br s, $C_4{}^4$—CH=N), 141.5 (br s, CH=N), 152.5 (s, $C_4{}^1$), 153.0 (br s, $C_0{}^1$, $C_1{}^1$, $C_2{}^1$, $C_3{}^1$).

UV-vis ($H_2O$): $\lambda_{max}$ ($\epsilon$, $M^{-1}\times cm^{-1}$) 286 nm (3.3×10$^6$).

General Procedures for Synthesizing the Products of the 3-[$G_n$] Type

A normal sodium hydroxide solution (n=1, 372 ml, 0.37 mmol; n=2, 312 ml, 0.31 mmol; n=3, 288 ml, 0.29 mmol; n=4, 288 ml, 0.28 mmol; n=5, 288 ml, 0.28 mmol) was added dropwise to a solution containing 100 mg of dendrimer 2-[$G_n$] in 30 ml of distilled water (n=1, 31 mmol; n=2, 13 mmol; n=3, 6 mmol; n=4, 3 mmol; n=5, 1.5 mmol), with vigorous stirring. The precipitate was isolated by centrifugation and dissolved in chloroform, and the organic layer was then dried on sodium sulfate. Finally, the product is filtered and dried by evaporation.

Dendrimer 3-[$G_1$] (yield=80%):

$^{31}P$ {$^1H$} NMR (CDCl$_3$): δ=8.2 ($P_0$), 68.3 ($P_1$).

$^1H$ NMR (CD$_2$Cl$_2$): δ=0.9 (t, $^3J_{HP1}$=7.0 Hz, 72H, CH$_2$CH$_3$), 2.3–2.5 (m, 72H, CH$_2$—N(CH$_2$—CH$_3$)$_2$), 2.9 (m, 24H, CH$_2$—N—P$_1$), 3.1 (d, $^3J_{HP1}$=9.4 Hz, 18H, CH$_3$N—P$_1$), 4.0 (m, 12H, N—H), 6.9 (d, $^3J_{HH}$=8.5 Hz, 12H, $C_0^2$—H), 7.5 (s, 6H, CH=N), 7.5 (d, $^3J_{HH}$=8.5 Hz, 12H, $C_0^3$—H).

$^{13}C$ {$^1H$} NMR (CDCl$_3$): δ=11.4 (s, CH$_2$CH$_3$), 30.5 (d, $^2J_{CP1}$=10.7 Hz, CH$_3$—N—P$_1$), 38.4 (s, CH$_2$—N—P$_1$), 46.3 (s, CH$_2$CH$_3$), 52.9 (d, $^3J_{CP1}$=7.8 Hz, CH$_2$—CH$_2$—N—P$_1$), 120.8 (s, $C_0^2$), 127.3 (s, $C_0^3$), 132.7 (s, $C_0^4$) 135.4 (d, $^3J_{CP1}$=12.5 Hz, CH=N), 150.4 (d, $^2J_{CP0}$=5.1 Hz, $C_0^1$).

Dendrimer 3-[$G_2$] (yield=95%):

$^{31}P$ {$^1H$} NMR (CDCl$_3$): δ=8.4 ($P_0$), 62.9 ($P_1$), 68.1 ($P_2$).

$^1H$ NMR (CD$_2$Cl$_2$): δ=0.9 (t, $^3J_{HH}$=7 Hz, 144H, CH$_2$CH$_3$), 2.2–2.5 (m, 144H, CH$_2$—N(CH$_2$—CH$_3$)$_2$), 2.9 (m, 48H, CH$_2$—N—P$_2$), 3.0 (d, $^3J_{HP2}$=9.2 Hz, 36H, CH$_3$N—P$_2$), 3.2 (d, $^3J_{HP1}$=10 Hz, 18H, CH$_3$—N—P$_1$), 4.0 (br m, 24H, N—H), 6.9–7.1 (m, 36H, $C_0^2$—H, $C_1^2$—H), 7.4–7.7 (m, 54H, CH=N, $C_0^3$—H, $C_1^3$—H).

$^{13}C$ {$^1H$} NMR (CDCl$_3$): δ=11.4 (s, CH$_2$CH$_3$), 30.6 (d, $^2J_{CP2}$=10.8 Hz, CH$_3$—N—P$_2$), 32.9 (d, $^2J_{CP1}$=11.8 Hz, CH$_3$—N—P$_1$), 38.3 (s, CH$_2$—N—P$_2$), 46.3 (s, CH$_2$CH$_3$), 52.9 (d, $^3J_{CP2}$=7.8 Hz, CH$_2$—CH$_2$—N—P$_2$), 121.1 (s, $C_0^2$, $C_1^2$), 127.4 (s, $C_1^3$), 128.1 (s, $C_0^3$), 132.0 (s, $C_0^4$), 133.1 (S, $C_1^4$), 135.1 (d, $^3J_{CP2}$=12.4 Hz, CH=N), 138.6 (d, $^3J_{CP1}$=15.4 Hz, CH=N), 150.3 (d, $^2J_{CP2}$=7.3 Hz, $C_1^1$), 151.1 (s, $C_0^1$).

Dendrimer 3-[$G_3$] (yield=95%):

$^{31}P$ {$^1H$} NMR (CDCl$_3$): δ=8.5 ($P_0$), 62.9 ($P_{1,2}$), 68.1 ($P_3$).

$^1H$ NMR (CD$_2$Cl$_2$): δ=0.9 (t, $^3J_{HH}$=6.4 Hz, 288H, CH$_2$CH$_3$), 2.2–2.5 (br m, 288H, CH$_2$—N(CH$_2$CH$_3$)$_2$), 2.9 (br m, 96H, CH$_2$—N—P$_3$), 3.0 (d, $^3J_{HP3}$=9.2 Hz, 72H, CH$_3$—N—P$_3$), 3.2–3.4 (br m, 54H, CH$_3$—N—P$_{1,2}$), 4.0 (br s, 48H, N—H), 6.9–7.3 (br m, 84H, $C_0^2$—H, $C_1^2$—H, $C_2^2$—H), 7.4–7.7 (br m, 126H, CH=N, $C_0^3$—H, $C_1^3$—H, $C_2^3$—H).

$^{13}C$ {$^1H$} NMR (CDCl$_3$): δ 11.4 (s, CH$_2$CH$_3$), 30.6 (d, $^2J_{CP3}$=10.3 Hz, CH$_3$—N—P$_3$), 32.5 (d, $^2J_{CP}$=12.7 Hz, CH$_3$—N—P$_{1,2}$), 38.4 (s, CH$_2$—N—P$_3$), 46.4 (s, CH$_2$CH$_3$), 53.0 (d, $^3J_{CP3}$=7.9 Hz, CH$_2$—CH$_2$—N—P$_3$), 121.4 (s, $C_0^2$, $C_1^2$, $C_2^2$), 127.5 (s, $C_2^3$), 128.2 (s, $C_0^3$, $C_1^3$), 132.0 (s, $C_0^4$), 132.3 (s, $C_1^4$), 133.1 (s, $C_2^4$), 135.2 (d, $^3J_{CP3}$=12.1 Hz, CH=N), 138.8 (d, $^3J_{CP3}$=12.1 Hz, CH=N), 150.4 (d, $^2J_{CP3}$=6.8 Hz, $C_2^1$), 151.2 (d, $^2J_{CP}$=6.3 Hz, $C_0^1$, $C_1^1$).

Dendrimer 3-[$G_4$] (yield=95%):

$^{31}P$ {$^1H$} NMR (CDCl$_3$): δ=8.4 ($P_0$), 62.4 ($P_{1,2,3}$), 68.0 ($P_4$).

$^1H$ NMR (CD$_2$Cl$_2$): δ=0.8 (br s, 576H, CH$_2$CH$_3$), 2.4 (br s, 576H, CH$_2$—N(CH$_2$CH$_3$)$_2$), 2.6–3.4 (br m, 462H, CH$_3$—N—P$_{1,2,3,4}$, CH$_2$—N—P$_4$), 4.0 (br m, 96H, N—H), 7.0–7.7 (m, 450H, $C_6H_4$, CH=N).

$^{13}C$ {$^1H$} NMR (CDCl$_3$): δ=11.6 (s, CH$_2$CH$_3$), 30.6 (d, $^2J_{CP4}$=10.4 Hz, CH$_3$—N—P$_4$), 33.0 (d, $^2J_{CP}$=12.6 Hz, CH$_3$—N—P$_{1,2,3}$), 38.5 (s, CH$_2$—N—P$_4$), 46.4 (s, CH$_2$CH$_3$), 53.1 (d, $^3J_{CP4}$=7.7 Hz, CH$_2$—CH$_2$—N—P$_4$), 121.5 (s, $C_3^2$), 121.8 (s, $C_0^2$, $C_1^2$, $C_2^2$), 127.5 (s, $C_3^3$), 128.3 (s, $C_0^3$, $C_1^3$, $C_2^3$), 132.2 (s, $C_0^4$, $C_1^4$, $C_2^4$), 133.2 (s, $C_3^4$), 135.1 (d, $^3J_{CP4}$=12.0 Hz, CH=N), 138.7 (br s, CH=N), 150.5 (d, $^2J_{CP2}$=7.4 Hz, $C_3^1$), 151.3 (br m, $C_0^1$, $C_1^1$, $C_2^1$).

Dendrimer 3-[$G_5$] (yield=95%):

$^{31}P$ {$^1H$} NMR (CDCl$_3$): δ=62.4 ($P_{1,2,3,4}$), 68.0 ($P_5$).

$^1H$ NMR (CD$_2$Cl$_2$): δ=1.0 (br s, 1152H, CH$_2$CH$_3$), 2.4 (br s, 1152H, CH$_2$—N(CH$_2$CH$_3$)$_2$), 2.7–3.5 (br m, 942H, CH$_3$—N—P$_{1,2,3,4,5}$, CH$_2$—N—P$_5$), 4.1 (m, 192H, N—H), 7.0–7.8 (m, 930H, $C_6H_4$, CH=N).

$^{13}C$ {$^1H$} NMR (CDCl$_3$): δ=11.5 (s, CH$_2$CH$_3$), 30.5 (d, $^2J_{CP5}$=11.1 Hz, CH$_3$—N—P$_5$), 33.0 (d, $^2J_{CP}$=12.3 Hz, CH$_3$—N—P$_{1,2,3,4}$), 38.4 (s, CH$_2$—N—P$_5$), 49.4 (s, CH$_2$CH$_3$), 53.0 (d, $^3J_{CP5}$=8.1 Hz, CH$_2$—CH$_2$—N—P$_5$), 121.4 (s, $C_4^2$), 121.7 (s, $C_0^2$, $C_1^2$, $C_2^2$, $C_3^2$), 127.4 (s, $C_4^3$), 128.1 (s, $C_0^3$, $C_1^3$, $C_2^3$, $C_3^3$), 132.1 (s, $C_0^4$, $C_1^4$, $C_2^4$, $C_3^4$), 133.1 (s, $C_4^4$) 135.1 (d, $^3J_{CP5}$=12.1 Hz, CH=N), 138.7 (br s, CH=N), 150.5 (d, $^2J_{CP3}$=6.6 Hz, $C_4^1$), 151.2 (d, $^2J_{CP}$=6.2 Hz, $C_0^1$, $C_1^1$, $C_2^1$, $C_3^1$).

General Procedures for Synthesizing the Products of the 4-[$G_n$] Type

A solution comprising 100 mg of neutral dendrimers 3-[$G_n$] (n=1, 36 mmol; n=2, 15 mmol; n=3, 7 mmol; n=4, 3.3 mmol; n=5, 1.6 mmol) and methyl iodide (n=1, 27 μl, 0.43 mmol; n=2, 22 μl, 0.36 mmol; n=3, 21 μl, 0.34 mmol; n=4, 20 μl, 0.32 mmol; n=5, 19 μl, 0.31 mmol) in 15 ml of DMF was stirred overnight at room temperature. The solution was dried by evaporation. The paste obtained was washed with 20 ml of a pentane/ether (1/1, v/v) mixture so as to obtain a yellow powder of methylated dendrimers named 4-[$G_n$].

Dendrimer 4-[$G_1$] (yield=90%):

$^{31}P$ {$^1H$} NMR (d$_6$-DMSO): δ=7.3 ($P_0$), 68.1 ($P_1$).

$^1H$ NMR (d$_6$-DMSO): δ=1.3 (t, $^3J_{HH}$=6.4 Hz, 72H, CH$_2$CH$_3$), 3.1 (s, 36H, $^+$N—CH$_3$), 3.2 (d, $^3J_{HP1}$=10.4 Hz, 18H, CH$_3$—N—P$_1$), 3.3–3.7 (br s, 96H, CH$_2$), 5.5 (br m, 12H, N—H), 7.1 (d, J$_{HH}$=8.1 Hz, 12H, $C_0^3$—H), 8.0 (s, 6H, CH=N), 8.0 (d, $^3J_{HH}$=8.1 Hz, 12H, $C_0^3$—H).

$^{13}C$ {$^1H$} NMR (d$_6$-DMSO): δ=7.8 (s, CH$_2$CH$_3$), 32.6 (d, $^2J_{CP1}$=9.5 Hz, CH$_3$—N—P$_1$), 34.9 (s, CH$_2$—N—P$_1$), 47.3 (s, $^+$N—CH$_3$), 56.4 (s, CH$_2$CH$_3$), 58.8 (s, CH$_2$—CH$_2$—N—P$_1$), 120.7 (s, $C_0^2$), 128.3 (s, $C_0^3$), 133.2 (s, $C_0^4$), 137.4 (d, $^3J_{CP1}$=14.2 Hz, CH=N), 149.9 (s, $C_0^1$).

Dendrimer 4-[$G_2$] (quantitative yield):

$^{31}P$ {$^1H$} NMR (d$_6$-DMSO): δ=7.3 ($P_0$), 61.7 ($P_1$), 68.1 ($P_2$).

$^1H$ NMR (d$_6$-DMSO): δ=1.3 (t, $^3J_{HH}$=6.2 Hz, 144H, CH$_2$CH$_3$), 3.1 (s, 72H, $^+$N—CH$_3$), 3.2–3.6 (m, 246H, CH$_3$—N—P$_{1,2}$, CH$_2$), 5.7 (br s, 24H, N—H), 7.0–7.4 (m, 36H, $C_0^2$—H, $C_1^2$—H), 7.7–8.2 (m, 54H, CH=N, $C_0^3$—H, $C_1^3$—H).

$^{13}C$ {$^1H$} NMR (d$_6$-DMSO): δ=7.8 (s, CH$_2$CH$_3$), 32.2 (d, $^2J_{CP2}$=8.9 Hz, CH$_3$—N—P$_2$), 33.5 (d, $^2J_{CP1}$=12.9 Hz, CH$_3$—N—P$_1$), 34.9 (s, CH$_2$—N—P$_2$), 47.3 (s, +N—CH$_3$), 56.4 (s, CH$_2$CH$_3$), 58.8 (d, $^3J_{CP2}$=3.3 Hz, CH$_2$—CH$_2$—N—P$_2$), 121.3 (s, $C_1^2$, $C_0^2$), 128.2 (s, $C_1^3$), 128.6 (s, $C_0^3$), 132.3 (s, $C_0^4$), 133.2 (s, $C_1^4$), 137.1 (d, $^3J_{CP2}$=12.3 Hz, CH=N), 140.7 (br s, CH=N), 150.1 (d, $^2J_{CP1}$=6 Hz, $C_1^1$), 150.5 (s, $C_0^1$).

Dendrimer 4-[$G_3$] (quantitative yield):

$^{31}P$ {$^1H$} NMR (d$_6$-DMSO): δ=6.9 ($P_0$), 61.9 ($P_{1,2}$), 68.1 ($P_3$).

$^1H$ NMR (d$_6$-DMSO): δ=1.3 (br s, 288H, CH$_2$CH$_3$), 3.1 (s, 144H, $^+$N—CH$_3$), 3.1–3.6 (m, 510H, CH$_3$—N—P$_{1,2,3}$, CH$_2$), 5.5 (br s, 48H, N—H), 7.0–7.4 (m, 84H, $C_0^2$—H, $C_1^2$—H, $C_2^2$—H), 7.7–8.2 (m, 126H, CH=N, $C_0^3$—H, $C_1^3$—H, $C_2^3$—H).

$^{13}C$ {$^1H$} NMR (d$_6$-DMSO): δ=7.7 (s, CH$_2$CH$_3$), 32.2 (d, $^2J_{CP3}$=9.4 Hz, CH$_3$—N—P$_3$), 33.5 (m, CH$_3$—N—P$_{1,2}$), 34.9 (s, CH$_2$—N—P$_3$), 47.3 (s, $^+$N—CH$_3$), 56.4 (s, CH$_2$CH$_3$), 58.8 (d, $^3J_{CP3}$=4.8 Hz, CH$_2$—CH$_2$—N—P$_3$), 121.0 (br s, $C_0^2$, $C_1^2$, $C_2^2$), 128.5 (br s, $C_0^3$, $C_1^3$, $C_2^3$), 132.3

(s, $C_0^4$, $C_1^4$), 133.2 (s, $C_2^4$), 137.1 (d, $^3J_{CP3}$=12.1 Hz, CH=N), 141.0 (br s, CH=N), 150.1 (d, $^2J_{CP2}$=6.2 Hz, $C_2^1$), 150.7 (br s, $C_0^1$, $C_1^1$).

Dendrimer 4-[G$_4$] (quantitative yield):

$^{31}$P {$^1$H} NMR (d$_6$-DMSO): δ=6.3 (P$_0$), 61.6 (P$_{1,2,3}$), 68.0 (P$_4$).

$^1$H NMR (d$_6$-DMSO): δ=1.3 (br s, 576H, CH$_2$CH$_3$), 3.1 (s, 288H, $^+$N—CH$_3$, 3.1–3.6 (m, 1038H, CH$_3$—N—P$_{1,2,3,4}$, CH$_2$), 5.5 (br s, 96H, N—H), 7.1–8.5 (m, 450H, C$_6$H$_4$, CH=N).

$^{13}$C {$^1$H} NMR (d$_6$-DMSO): δ=7.8 (s, CH$_2$CH$_3$), 32.2 (d, $^2J_{CP4}$=9.5 Hz, CH$_3$—N—P$_4$), 33.6 (d, $^2J_{CP}$=7.6 Hz, CH$_3$—N—P$_{1,2,3}$), 34.9 (s, CH$_2$—N—P$_4$), 47.3 (s, $^+$N—CH$_3$), 56.4 (s, CH$_2$CH$_3$), 58.7 (d, $^3J_{CP4}$=4.8 Hz, CH$_2$—CH$_2$—N—P$_4$), 121.2 (br s, $C_0^2$, $C_1^2$, $C_2^2$, $C_3^2$), 128.2 (br s, $C_0^3$, $C_1^3$, $C_2^3$, $C_3^3$), 132.2 (s, $C_0^4$, $C_1^4$, $C_2^4$), 133.2 (s, $C_3^4$), 137.1 (d, $^3J_{CP4}$=9.4 Hz, CH=N), 140.8 (br s, CH=N), 150.0 (d, $^2J_{CP2}$=6.2 Hz, $C_3^1$), 150.7 (br s, $C_0^1$, $C_1^1$, $C_2^1$).

Dendrimer 4-[G$_5$] (quantitative yield):

$^{31}$P {$^1$H} NMR (d$_6$-DMSO): δ=61.6 (P$_{1,2,3,4}$), 68.0 (P$_5$).

$^1$H NMR (d$_6$-DMSO): δ=1.3 (br s, 1152H, CH$_2$CH$_3$), 3.1 (s, 576H, $^+$N—CH$_3$), 3.1–3.6 (m, 2094H, CH$_3$—N—P$_{1,2,3,4,5}$, CH$_2$), 5.4 (m, 192H, N—H), 7.2–8.5 (m, 930H, C$_6$H$_4$, CH=N). $^{13}$C {$^1$H} NMR (d$_6$-DMSO): δ=7.8 (s, CH$_2$CH$_3$), 32.3 (br s, CH$_3$—N—P$_5$), 33.5 (br s, CH$_3$—N—P$_{1,2,3,4}$), 34.9 (s, CH$_2$—N—P$_5$), 47.3 (s, $^+$N—CH$_3$), 56.4 (s, CH$_2$CH$_3$), 58.8 (d, $^3J_{CP}$= 5.0 Hz, CH$_2$—CH$_2$—N—P$_5$), 121.3 (br s, $C_0^2$, $C_1^2$, $C_2^2$, $C_3^2$, $C_4^2$), 128.2 (br s, $C_0^3$, $C_1^3$, $C_2^3$, $C_3^3$, $C_4^3$), 132.2 (s, $C_0^4$, $C_1^4$, $C_2^4$, $C_3^4$), 133.2 (s, $C_4^4$), 137.2 (d, $^3J_{CP4}$=9.7 Hz, CH=N), 141.2 (br s, CH=N), 150.1 (d, $^2J_{CP2}$=6.0 Hz, $C_4^1$), 150.7 (br s, $C_0^1$, $C_1^1$, $C_2^1$, $C_3^1$).

General Procedures for Synthesizing the Products of the 5-[G$_n$]Type

The resin with a high capacity for anion exchange, AG1-X8, was added to a suspension of 100 mg of methylated dendrimers 4-[G$_n$] (in the form of iodides) (n=1, 22 μmol; n=2, 10 μmol; n=3, 4.7 μmol; n=4, 21 μmol; n=5, 1.1 μmol) in distilled water (n=1, 25 ml; n=2, 23 ml; n=3, 22 ml; n=4, 21 ml; n=5, 20 ml), in the proportions indicated (n=1, 1.24 g; n=2, 1.13 g; n=3, 1.06 g; n=4, 1.03 g; n=5, 1 g), and mixed gently for one hour. The paste obtained was washed with 20 ml of a pentane/ether (1/1, v/v) mixture so as to obtain a white powder of methylated dendrimers, in acetate form, named 5-[G$_n$]. 8 to 10% of the terminal branches are modified during the counter-ion exchange with the resin and were provisionally attributed to a demethylated form since the NMR results were identical to those of the neutral dendrimers bearing tertiary amines (3-[G$_n$]). These minor terminal branches were indicated with an asterisk in the NMR results present below and the yields correspond to those of the total dendrimer.

Dendrimer 5-[G$_1$] (yield 90%):

$^{31}$P {$^1$H} NMR (CD$_3$OD): δ=7.8 (P$_0$), 69.8 (P$_1$*), 70.3 (P$_1$).

$^1$H NMR (d$_6$-DMSO): δ=1.0 (t, $^3J_{HH}$=6.9 Hz, 6H, CH$_2$CH$_3$*), 1.3 (t, $^3J_{HH}$=6.5 Hz, 66H, CH$_2$CH$_3$), 1.7 (s, 33H, CH$_3$COO$^-$), 2.5 (m, 6H, CH$_2$*-N(CH$_2$*CH$_3$)$_2$), 3.1 (s, 33H, $^+$N—CH$_3$), 3.2 (d, $^3J_{HP1}$=8.3 Hz, 18H, CH$_3$—N—P$_1$), 3.3–3.7 (m, 90H, CH$_2$), 7.1 (d, $^3J_{HH}$=8.3 Hz, 12H, $C_0^2$—H), 7.6 (b, 12H, N—H), 7.8 (s, 6H, CH=N), 7.8 (d, $^3J_{HH}$=8.3 Hz, 12H, $C_0^3$—H).

$^{13}$C {$^1$H} NMR (d$_6$-DMSO): δ=7.6 (s, CH$_2$CH$_3$), 11.9 (s, CH$_2$C*H$_3$), 25.6 (s, CH$_3$COO$^-$), 32.2 (d, $^2J_{CP1}$=9.5 Hz, CH$_3$—N—P$_1$), 38.8 (s, CH$_2$—N—P$_1$), 46.6 (s, C*H$_2$CH$_3$), 47.0 (s, $^+$N—CH$_3$), 54.5 (s, C*H$_2$—CH$_2$—N—P$_1$), 56.2 (s, CH$_2$CH$_3$), 59.1 (d, $^3J_{CP1}$=5.3 Hz, CH$_2$—CH$_2$—N—P$_1$), 120.6 (s, $C_0^2$), 127.9 (s, $C_0^3$), 133.7 (s, $C_0^4$), 135.8 (d, $^2J_{CP0}$=10.8 Hz, CH=N), 149.8 (s, $C_0^1$), 173.7 (s, CH$_3$COO$^-$).

UV-vis (H$_2$O): λ$_{max}$ (ϵ, M$^{-1}$×cm$^{-1}$) 284 nm (1.2×10$^5$).

Dendrimer 5-[G$_2$] (yield=95%):

$^{31}$P {$^1$H} NMR (CD$_3$OD): δ=8.4 (P$_0$), 62.3 (P$_1$), 69.5 (P$_2$*), 70.1 (P$_2$).

$^1$H NMR (d$_6$-DMSO): δ=1.0 (br t, 12H, CH$_2$CH$_3$*), 1.3 (br s, 132H, CH$_2$CH$_3$), 1.7 (s, 66H, CH$_3$COO$^-$), 2.5 (br m, 12H, CH$_2$*-N(CH$_2$*CH$_3$)$_2$), 3.1 (s, 66H, $^+$N—CH$_3$), 3.2–3.6 (m, 234H, CH$_3$—N—P$_{1,2}$, CH$_2$) 7.1–7.3 (br m, 36H, $C_0^2$—H, $C_1^2$—H), 7.6 (br s, 24H, N—H), 7.7 (s, 12H, CH=N), 7.8–8.1 (br m, 42H, CH=N, $C_0^3$—H, $C_1^3$—H).

$^{13}$C {$^1$H} NMR (d$_6$-DMSO): δ=7.6 (s, CH$_2$CH$_3$), 11.9 (s, CH$_2$C*H$_3$), 25.6 (S, CH$_3$COO$^-$), 32.1 (d, $^2J_{CP2}$=9.3 Hz, CH$_3$—N—P$_2$), 33.2 (d, $^2J_{CP1}$=13.4 Hz, CH$_3$—N—P$_1$), 35.0 (s, CH$_2$—N—P$_2$), 46.6 (s, C*H$_2$CH$_3$), 47.0 (s, $^+$N—CH$_3$), 54.5 (s, C*H$_2$—CH$_2$—N—P$_2$), 56.2 (s, CH$_2$CH$_3$), 59.1 (d, $^3J_{CP2}$=5.3 Hz, CH$_2$—CH$_2$—N—P$_2$), 121.3 (s, $C_0^2$, $C_1^2$), 127.9 (s, $C_1^3$), 128.5 (s, $C_0^3$), 132.3 (s, $C_0^4$), 133.8 (s, $C_1^4$), 135.7 (br s, CH=N), 149.8 (d, $^2J_{CP1}$=6.5 Hz, $C_1^1$), 150.7 (s, $C_0^1$), 173.7 (s, CH$_3$COO$^-$).

UV-vis (H$_2$O): λ$_{max}$ (ϵ, M$^{-1}$×cm$^{-1}$) 284 nm (4.1×10$^5$).

Dendrimer 5-[G$_3$] (yield=95%):

$^{31}$P {$^1$H} NMR (CD$_3$OD): δ=8.4 (P$_0$), 62.3 (P$_{1,2}$), 69.5 (P$_3$*), 70.1 (P$_3$).

$^1$H NMR (d$_6$-DMSO): δ=1.0 (br t, 30H, CH$_2$CH$_3$*), 1.3 (br s, 258H, CH$_2$CH$_3$), 1.7 (s, 129H, CH$_3$COO$^-$), 2.5 (br m, 30H, CH$_2$*-N(CH$_2$*CH$_3$)$_2$), 3.1 (s, 129H, $^+$N—CH$_3$), 3.1–3.6 (m, 480H, CH$_3$—N—P$_{1,2,3}$, CH$_2$) 7.1–7.5 (br m, 108H, $C_0^2$—H, $C_1^2$—H, $C_2^2$—H, N—H), 7.5–8.1 (br m, 126H, CH=N, $C_0^3$—H, $C_1^3$—H, $C_2^3$—H).

$^{13}$C {$^1$H} NMR (d$_6$-DMSO): δ=7.6 (s, CH$_2$CH$_3$), 11.9 (s, CH$_2$C*H$_3$), 25.2 (s, CH$_3$COO$^-$), 32.1 (d, $^2J_{CP3}$=9.0 Hz, CH$_3$—N—P$_3$), 33.2 (br m, CH$_3$—N—P$_{1,2}$), 35.0 (s, CH$_2$—N—P$_3$), 46.6 (s, C*H$_2$CH$_3$), 47.1 (s, $^+$N—CH$_3$), 54.5 (s, C*H$_2$—CH$_2$—N—P$_3$), 56.3 (s, CH$_2$CH$_3$), 59.1 (d, $^3J_{CP3}$=5.7 Hz, CH$_2$—CH$_2$—N—P$_3$), 121.3 (br s, $C_0^2$, $C_1^2$, $C_2^2$), 128.0 (s, $C_2^3$), 128.5 (S, $C_0^3$, $C_1^3$), 132.4 (s, $C_0^4$, $C_1^4$), 133.8 (s, $C_2^4$), 136.3 (br d, $C_2^4$—CH=N), 141.0 (br m, CH=N), 150.1 (d, $^2J_{CP2}$=6.3 Hz, $C_2^1$), 151.0 (d, $^2J_{CP}$=7.1 Hz, $C_0^1$, $C_1^1$), 173.7 (s, CH$_3$COO$^-$).

UV-vis (H$_2$O): λ$_{max}$ (ϵ, M$^{-1}$×cm$^{-1}$) 286 nm (7.4×10$^5$).

Dendrimer 5-[G$_4$] (yield=95%):

$^{31}$P {$^1$H} NMR (CD$_3$OD): δ=8.2 (P$_0$), 62.2 (P$_{1,2,3}$), 69.9 (P$_4$).

$^1$H NMR (d$_6$-DMSO): δ=1.0 (br m, 60H, CH$_2$CH$_3$*), 1.3 (br s, 516H, CH$_2$CH$_3$), 1.7 (s, 258H, CH$_3$COO$^-$), 2.5 (m, 60H, CH$_2$*-N(CH$_2$*CH$_3$)$_2$), 3.1 (s, 258H, $^+$N—CH$_3$), 3.1–3.6 (m, 978H, CH$_3$—N—P$_{1,2,3,4}$, CH$_2$) 7.0–8.2 (m, 546H, C$_6$H$_4$, CH=N, N—H).

$^{13}$C {$^1$H} NMR (d$_6$-DMSO): δ=7.6 (s, CH$_2$CH$_3$), 11.9 (s, CH$_2$C*H$_3$), 24.7 (s, CH$_3$COO$^-$), 32.1 (d, $^2J_{CP4}$=9.6 Hz, CH$_3$—N—P$_4$), 33.2 (d, $^2J_{CP}$=11.2 Hz, CH$_3$—N—P$_{1,2,3}$), 35.0 (s, CH$_2$—N—P$_4$), 46.6 (s, C*H$_2$CH$_3$), 47.0 (s, $^+$N—CH$_3$), 54.5 (d, $^3J_{CP4}$=3.9 Hz, C*H$_2$—CH$_2$—N—P$_4$), 56.3 (s, CH$_2$CH$_3$), 59.2 (d, $^3J_{CP4}$=5.7 Hz, CH$_2$—CH$_2$—N—P$_4$), 121.2 (s, $C_3^2$), 121.6 (s, $C_0^2$, $C_1^2$, $C_2^2$), 127.9 (s, $C_3^3$), 128.5 (s, $C_0^3$, $C_1^3$, $C_2^3$), 132.3 (s, $C_0^4$, $C_1^4$, $C_2^4$), 133.7 (s, $C_3^4$), 135.8 (br s, $C_3^4$—CN=N), 141.0 (br s, CH=N), 149.9 (d, $^2J_{CP3}$=6.3 Hz, $C_3^1$), 151.0 (br m, CO$_0^1$, $C_1^1$, $C_2^1$), 173.7 (s, CH$_3$COO$^-$).

UV-vis (H$_2$O): λ$_{max}$ (ϵ, M$^{-1}$×cm$^{-1}$) 288 nm (1.6×10$^6$).

Dendrimer 5-[G$_5$] (yield=95%):

$^{31}$P {$^1$H} NMR (d$_6$-DMSO): δ=62.2 (P$_{1,2,3,4}$), 69.9 (P$_5$).

$^1$H NMR (d$_6$-DMSO): δ=1.0 (m, 114H, CH$_2$CH$_3$*), 1.3 (m, 1038H, CH$_2$CH$_3$), 1.7 (s, 519H, CH$_3$COO$^-$), 2.5 (m,

114H, $CH_2*-N(CH_2*CH_3)_2$), 3.1 (s, 519H, $^+N-CH_3$), 3.1–3.6 (m, 1980H, $CH_3-N-P_{1,2,3,4,5}$, $CH_2$), 7.0–8.2 (m, 1122H, $C_6H_4$, CH=N, N—H).

$^{13}C$ {$^1H$} NMR ($d_6$-DMSO): δ=7.6 (s, $CH_2CH_3$), 11.9 (s, $CH_2C*H_3$), 24.7 (s, $CH_3COO^-$), 32.1 (d, $^2J_{CP5}$=9.6 Hz, $CH_3-N-P_5$), 33.2 (d, $^2J_{CP}$=11.2 Hz, $CH_3-N-P_{1,2,3,4}$), 35.0 (s, $CH_2-N-P_5$), 46.6 (s, $C*H_2CH_3$), 47.0 (s, $^+N-CH_3$), 54.5 (d, $^3J_{CP5}$=3.9 Hz, $C*H_2-CH_2-N-P_5$), 56.3 (s, $CH_2CH_3$), 59.2 (d, $^3J_{CP5}$=5.7 Hz, $CH_2-CH_2-N-P_5$), 121.2 (s, $C_0^2$, $C_1^2$, $C_2^2$, $C_3^2$, $C_4^2$), 127.9 (s, $C_4^3$), 128.5 (s, $C_0^3$, $C_1^3$, $C_2^3$, $C_3^3$), 132.3 (s, $C_0^4$, $C_1^4$, $C_2^4$, $C_3^4$), 133.7 (s, $C_4^4$), 135.9 (br s, $C_4^4$—CH=N), 141.0 (br s, CH=N), 149.9 (d, $^2J_{CP3}$= 6.5 Hz, $C_4^1$), 151.0 (br m, $C_0^1$, $C_1^1$, $C_2^1$, $C_3^1$), 173.7 (s, $CH_3COO^-$).

UV-vis ($H_2O$): $\lambda_{max}$ (ε, $M^{-1} \times cm^{-1}$) 284 nm ($3.7 \times 10^6$).

EXAMPLE 2

Transfection Experiments

The results obtained with these various polycationic phosphorus-containing dendrimers always showed optimum efficiency with an N/P charge ratio of between 5 (FIG. 4) and 10 (FIG. 5) (N/P ratio= number of terminal nitrogen atoms of the dendrimer per phosphate of the DNA). Thus, it was decided, in an arbitrary manner, to compare the transfection efficiency of various generations of phosphorus-containing dendrimers (P-dendrimers) with that of the linear PEI ExGen 500, having 5 to 10 amine equivalents per nucleotide.

Figure 4:
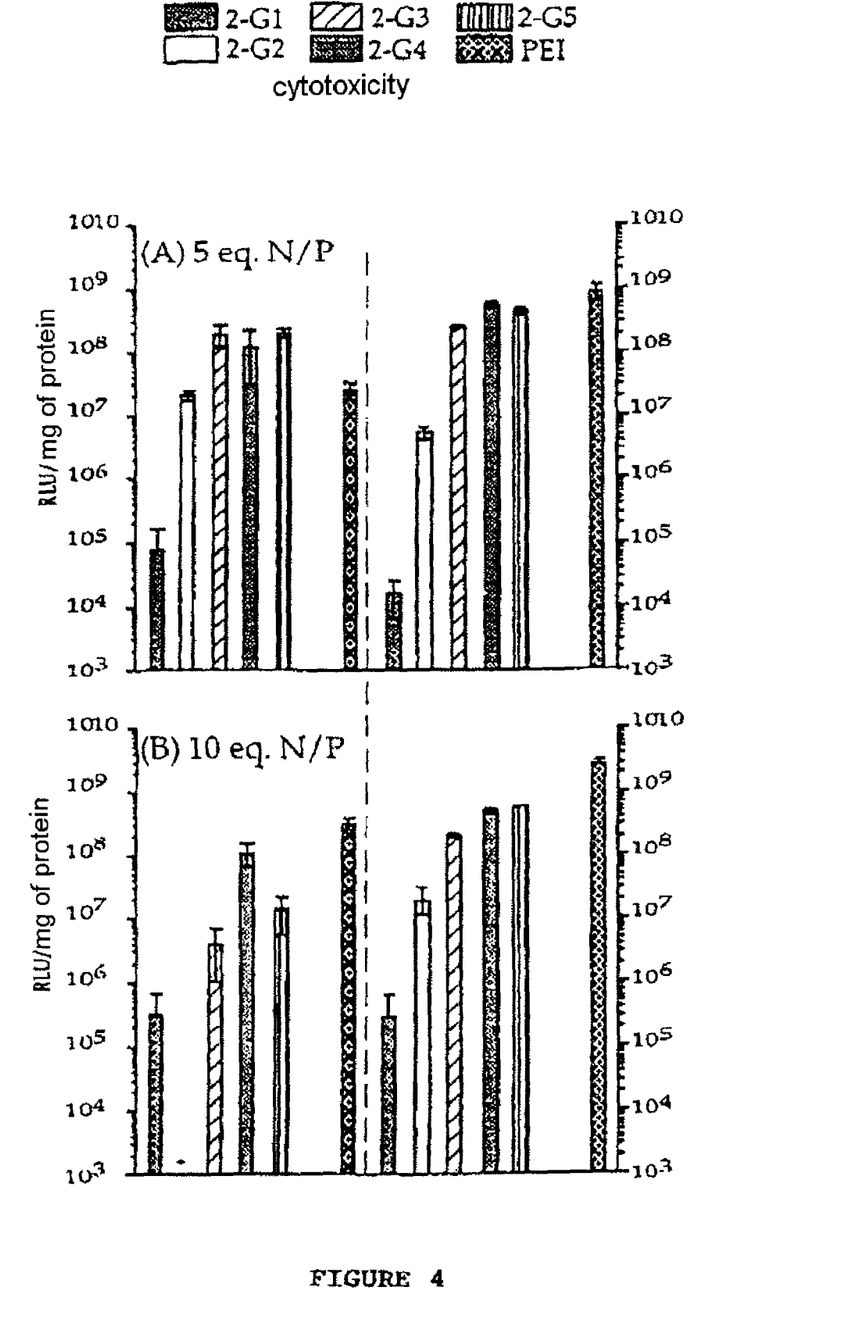
FIG. 4 illustrates the gene transfer properties of the dendrimers of the 2-[$G_n$] type, in the presence of serum (right-hand sections of FIGS. 4A and 4B) or in the absence of serum (left-hand sections of FIGS. 4A and 4B)
Figure 5:
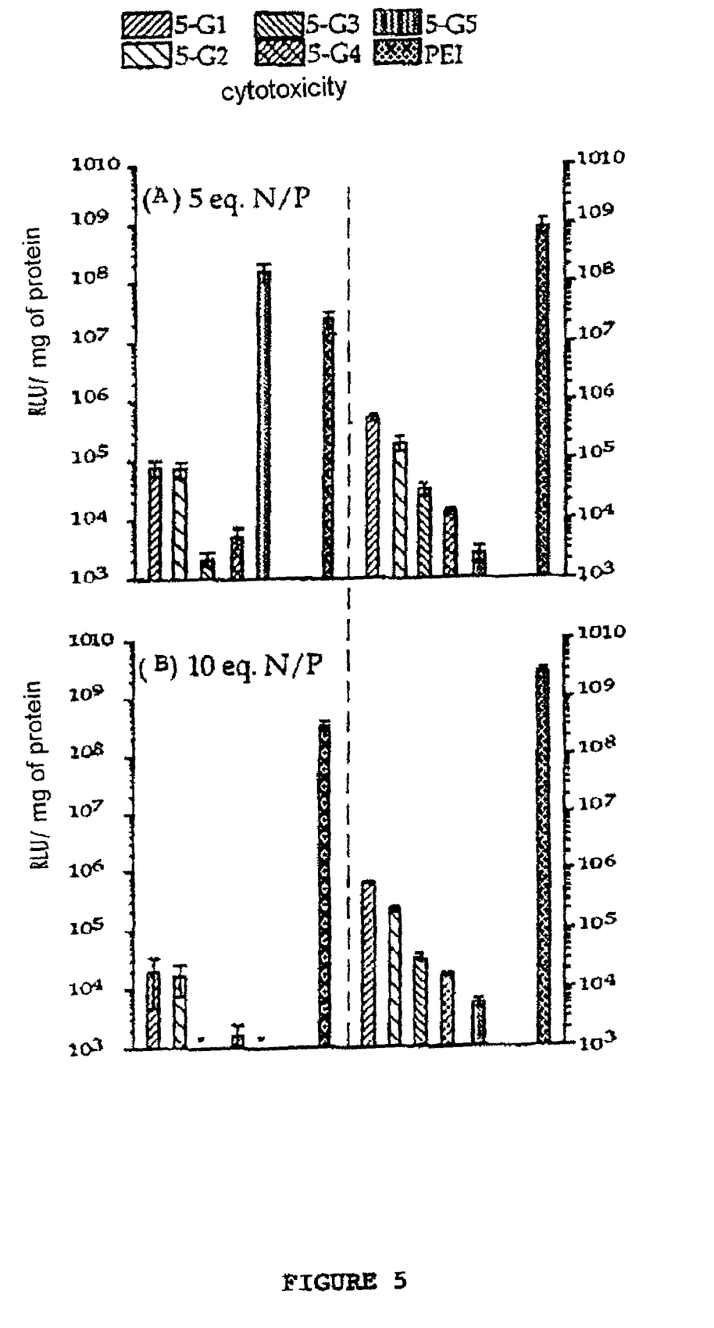
FIG. 5 illustrates the gene transfer properties of the dendrimers of the 5-[$G_n$] type, in the presence of serum (right-hand sections of FIGS. 5A and 5B) or in the absence of serum (left-hand sections of FIGS. 5A and 5B).

With 5 positive-charge equivalents per phosphate of the DNA, the 5 different generations of protonated dendrimers of the 2-[$G_n$] type, tested in the form of hydrochlorides, made it possible to obtain significant expression of the transgene. An increase of $10^5$ to almost $10^9$ relative light units (RLU)/mg of protein was observed. The transfection efficiency increases with the size of the dendrimer (generation number) but reaches a plateau from the third generation, with values of between $10^8$ ad $10^9$ RLU (FIG. 4). Consequently, 2-[$G_4$] was chosen to study in greater detail the transfection efficiency of these novel cationic phosphorus-containing dendrimers, the structure of which is given in FIG. 2.

It should be noted that the transfections performed in the presence of serum produce less toxicity. As a result, a higher level of expression is observed for the transfections performed in the presence of serum compared to those performed without serum (FIGS. 4A and 4B, right and left panels, respectively).

Without trying to further optimize their transfection conditions, the dendrimers of the third to the fifth generation prove to be as efficient as the linear PEI used under optimal conditions.

On the other hand, the methylated forms 5-[$G_n$] prove to be rather toxic and relatively inefficient for transfecting nucleic acids into eukaryotic cells (FIGS. 5A and 5B). This phenomenon may be explained by a stable positive charge density which may disturb the cell membrane and cause cell death. It is not possible to decrease the charge density of the methylated forms without degrading the dendrimer; on the other hand, the charge density of the chloride derivatives (2-[$G_n$]) may be modulated by microenvironmental modifications of the pH when they approach the cell membrane. In addition, the possibility of modulating the charge density of the chloride derivatives of the dendrimers may play a key role in the release of the luciferase gene from the endosome. These dendrimers perhaps behave like proton reservoirs in the cellular compartments, their charge density being controlled, firstly, by ATPase-coupled proton pumps and, secondly, by intracellular modifications of the chloride concentration. The possibility of decreasing the cationic charge density of these phosphorus-containing dendrimers, inside or outside the cells, would be an advantage for carrying out experiments in vivo, as previously mentioned (26).

Chemical Products

The linear 22 kDa PEI (ExGen 500) was supplied by Euromedex (Souffelweyersheim, France).

Cell Lines and Culture

The NIH3T murine fibroblasts come from the ATCC (Rockville, Mass., USA) and are cultured in Dulbecco modified Eagle medium (DMEM). The culture media are supplemented with 10% of fetal calf serum (D. Dutscher, Brunath, France), 2 mM of L-glutamine (Gibco-BRL), 100 units/ml of penicillin (Gibco-BRL) and 100 μg/ml of streptomycin (Gibco-BRL). The cells are maintained at 37° C., in a humid atmosphere containing 5% of $CO_2$. When the cells reach 80% confluency, they are detached with a saline solution of trypsin-EDTA (Gibco-BRL), diluted ten-fold and cultured in a new flask.

Plasmids

PCMV-luc, which encodes *Photinus pyralis* luciferase under the control of the promoter/enchancer sequences of the cytomegalovirus were kindly provided by Dr. M. Scarpa (CRIBI, Padoua, Italy). The plasmids were purified on Qiagen columns (Rockford, USA), from the transformed *E. coli* strain XL1.

Transfection of Cells

The adherence cells were seeded into 24-well plates (Costar, D. Dutscher, France) the day before transfection, so as to reach 60 to 70% confluency on the day of transfection. All the experiments were carried out in triplicate. The cells were rinsed before transfection and 1 ml of medium with or without serum was added to each well. 2 μg of plasmid (1.5 mg/ml solution in a 10 mM Tris-1 mM EDTA buffer, pH 7.4) were diluted in 50 μl of 0.15M NaCl.

The N/P (nitrogen/phosphate) ratio corresponds to the amount of polymer necessary to have one amine residue (43 Da=average molecular weight ($M_w$) for the PEI; for the dendrimers, the nitrogen molarity of the amine residues was calculated by dividing the $M_w$ by the number of charges for each generation) per nucleic acid phosphate ($M_w$330) (12). The required amount of linear PEI (ExGen500) and of dendrimers (from stock solutions of PEI and of dendrimers corresponding to 10 mM of nitrogen, in amine form, in sterile MilliQ water) was diluted in 50 μl of 0.15M NaCl, vortexed gently and centrifuged. After 15 min, the cationic vector was added, in a single step, to the plasmid solution [and not in the reverse order (12)] and the mixture was then vortexed and centrifuged. The amounts and volumes indicated above correspond to one well and were, in fact, multiplied by three and distributed into three wells. After 10 min, the mixture was added to the cells and the supernatant was distributed homogeneously by slight horizontal manual rotation. Immediately afterwards, the culture plate was centrifuged (Sigma 3K10, Bioblok, France) for 5 min at 1 500 rpm (280 g). After incubation for 2 to 3 hours, 110 μl of fetal calf serum were added to the wells without serum. The cells were cultured for 24 h and the expression of the reporter gene was then tested.

Luciferase Measurement

The expression of the luciferase gene was measured by luminescence. The culture medium was removed and the cell lysate was harvested after incubation for 30 min at room temperature in the 1× lysis buffer (Promega, USA). The lysate was gently vortexed and centrifuged at 140 000 rpm (17 530 g), for 5 min at 4° C. 20 µl of lysate were diluted in 100 µl of luciferase reaction buffer (Promega, USA) and the luminescence was measured for 10 sec (Mediators PhL, Vienna, Austria). Results were expressed as units of luminescence per mg of protein (measurement using the BCA test, Pierce).

EXAMPLE 3

Percentages of Viability of the Cells Transfected in Accordance with Example 2

| Dendrimers-N$^+$Et$_2$H, Cl$^-$ | | Dendrimers-N$^+$Et$_2$Me, CH$_3$CO$_2^-$ | |
|---|---|---|---|
| 5 equivalents | 10 equivalents | 5 equivalents | 10 equivalents |
| G$_1$ 95 | 105 | G$_1$ 90 | 88 |
| G$_2$ 91 | 83 | G$_2$ 91 | 101 |
| G$_3$ 83 | 90 | G$_3$ 87 | 99 |
| G$_4$ 94 | 91 | G$_4$ 99 | 95 |
| G$_5$ 90 | 80 | G$_5$ 108 | 92 |

Linear PEI: 5 equivalents: 69; 10 equivalents: 84 Crosslinked PEI: 5 equivalents: 102; 10 equivalents: 91

REFERENCES

[1] A. D. Miller, *Nature* 1992, 357, 455–460.
[2] J. M. Wilson, *New Engl. J. Med.* 1996, 334, 1185–1187.
[3] P. Briand, A. Kahn, *Path. Biol.* 1993, 41, 663–671.
[4] B. Y. Roessler, J. W. Hartman, D. K. Vallance, Y. M. Larta, J. L. Janich, B. L. Davidson, *Hum. Gene. Ther.* 1995, 6, 307–316.
[5] C. J. Wheeler, J. H. Felgner, Y. J. Tsai, J. Marshal, L. Sukhu, S. G. Doh, J. Hartikka, J. Nietsupski, M. Manthorpe, M. Nichols, M. Plewe, X. Liang, J. Norman, A. Smith, S. H. Cheng, *Proc. Natl. Acad. Sci. USA* 1996, 93, 11454–11459.
[6] J. P. Behr, *Bioconjugate Chem.* 1994, 5, 382–389.
[7] J. P. Vigneron, N. Oudrhiri, M. Fauquet, L. Vergely, J. C. Bradley, M. Bassville, P. Lehn, J. M. Lehn, *Proc. Natl. Acad. Sci. USA* 1996, 93, 9682–9686.
[8] G. Byk, C. Dubertret, V. Escriou, M. Frederic, G. Jaslin, R. Rangara, B. Pitard, J. Crouzet, P. Wils, B. Schwartz, D. Scherman, *J. Med. Chem.* 1998, 41, 224–235.
[9] A. W. Miller, *Angew. Chem. Inter. Ed. Engl.* 1998, 37, 1768–1785.
[10] T. Hara, Y. Tan, L. Huang, *Proc. Natl. Acad. Sci. USA* 1997, 94, 14547–14552.
[11] I. Koltover, T. Salditt, J. O. Rädler, C. R. Safinya *Science* 1998, 281, 78–81.
[12] O. Boussif, M. A. Zanta, A. Adib, J. P. Behr, *Gene Ther.* 1996, 3, 1074–1080.
[13] J. Haensler, F. C. Szoka, *Bioconjugate Chem.* 1993, 4, 372–379.
[14] A. Bielinska, J. F. Kukowska-Latallo, J. Johnson, D. A. Tomalia, J. R. Baker, *Nucleic Acids Res.* 1996, 24, 2176–2182.
[15] M. X. Tang, C. T. Redemann, F. C. Szoka, *Bioconjugate Chem.* 1996, 7, 703–714.
[16] N. Launay, A. M. Caminade, R. Lahana, J. P. Majoral, *Angew. Chem. Int. Ed. Engl.* 1994, 33, 1589–1592.
[17] N. Launay, A. M. Caminade, J. P. Majoral, *J. Am. Chem. Soc.* 1995, 117, 3282–3283.
[18] C. Galliot, C. Larré, A. M. Caminade, J. P. Majoral, *Science* 1997, 277, 1981–1984.
[19] C. Larré, B. Donnadieu, A. M. Caminade, J. P. Majoral, *J. Am. Chem. Soc.* 1998, 120, 4029–4030.
[20] D. A. Tomalia, H. D. Durst, *Topics Curr. Chem.* 1993, 165, 193–313.
[21] F. Zeng, S. C. Zimmerman, *Chem. Rev.* 1997, 97, 1681–1712.
[22] K. W. Pollak, J. W. Leon, J. M. J. Fréchet, M. Maskus, H. D. Abruna, *Chem. Mater.* 1998, 10, 30–38.
[23] E. Wagner, M. Cotten, R. Foisner, M. L. Birnstiel, *Proc. Natl. Acad. Sci. USA* 1991, 88, 4255–4259.
[24] E. Wagner, C. Plank, K. Zatloukal, M. Cotten, M. L. Birnstiel, *Proc. Natl. Acad. Sci. USA* 1992, 89, 7934–7938.
[25] J. F. Kukowska-Latallo, A. U. Bielinska, J. Johnson, R. Spindler, D. A. Tomalia, J. R. Baker, *Proc. Natl. Acad. Sci. USA* 1996, 93, 4897–4902.
[26] J. S. Remy, A. Kichler, V. Mordinov, F. Schuber, J. P. Behr, *Proc. Natl. Acad. Sci. USA* 1995, 92, 1744–1748.
[27] PCT international application WO 95/02397.
[28] D. Prévôté et al., *J. Org. Chem.,* 1997, 62, 14, 4834–4841.

As emerges from the above, the invention is in no way limited to its methods of implementation, preparation and application which has just been described more explicitly; on the contrary, it encompasses all the variants thereof which may occur to a person skilled in the art, without departing from the context or the scope of the present invention.

What is claimed is:

1. A polycationic phosphorus-containing dendrimer, which consists:
    of a central layer in the form of a central core $P_0$ comprising 2 to 8 functionalized groups,
    of n intermediate layers, which may be identical or different, each one of said intermediate layers consisting of units $P_1$ corresponding to formula II:

in which;
L is an oxygen, phosphorus or sulfur atom,
M represents one of the following groups:
    an aromatic group di-, tri- or tetra-substituted with alkyl, alkoxy or unsaturated $C_1$–$C_{12}$ olefinic, azoic or acetylenic groups, unsubstituted or substituted with at least one phosphorous, oxygen, nitrogen, sulfur or halogen atom, or
    an alkyl or alkoxy group comprising several substituents as defined when M is an aromatic group,
$R_1$ and $R_2$, which may be identical or different, represent a hydrogen atom or one of the following groups: alkyl, alkoxy, or aryl, unsubstituted or substituted with at least one phosphorous, oxygen, nitrogen, sulfur or halogen atom,
n is an integer between 1 and 11,
E is selected from the group consisting of an oxygen atom, a sulfur atom, a nitrogen atom and a nitrogen atom linked to an alkyl, alkoxy or aryl group,
    an outer layer consisting of units P2, which may be identical or different, corresponding to formula III:

(III)

(Ib)

in which:

$R_5$ represents a hydrogen atom or one of the following groups: alkyl, alkoxy, or aryl, unsubstituted or substituted with at least one phosphorus, oxygen, nitrogen, sulfur or halogen atom,

W represents one of the following groups: alkyl, alkoxy, or aryl, unsubstituted or substituted with at least one phosphorus, oxygen, nitrogen, sulfur or halogen atom, $R_3$ and $R_4$, which may be identical or different, represent a $C_1$–$C_5$ alkyl group, X represents a hydrogen atom or a $C_1$–$C_5$ alkyl group or is absent, and Z represents a halide ion, an alkylCOO$^-$ group or any other anionic group comprising carbon, oxygen, sulfur, nitrogen, phosphorus or halogen atoms, or is absent.

2. The dendrimer as claimed in claim 1, wherein the central core $P_0$ is selected from the group consisting of the group of general formula Ia:

(Ia)

and the group of general formula Ib:

3. The dendrimer as claimed in claim 1 or claim 2, wherein said dendrimer has terminal units of formula III, in which X represents a hydrogen atom, $R_5$ is a hydrogen atom, W represents a group $(CH_2)_2$, $R_3$ and $R_4$ are identical and represent ethyl groups, and Z is a chloride ion.

4. The dendrimer as claimed in claim 1 or claim 2, wherein said dendrimer has terminal units of formula III, in which X represents a methyl group, $R_5$ is a hydrogen atom, W represents a group $(CH_2)_2$, $R_3$ and $R_4$ are identical and represent ethyl groups, and Z is a group $CH_3COO^-$.

5. A composition capable of acting as an agent for transfecting a nucleic acid sequence into a eukaryotic cell, said composition comprising a nucleic acid and a polycationic phosphorus-containing dendrimer as claimed in claim 1, coupled to said nucleic acid.

6. The composition as claimed in claim 5, said composition further comprising at least one pharmaceutically acceptable vehicle.

7. The composition as claimed in claim 5 or claim 6, wherein the N/P ratio, in which N corresponds to the number of terminal nitrogen atoms of the dendrimer per phosphate (P) of said nucleic acid, is between 5 and 10.

8. The composition as claimed in claim 5, said composition further comprising an agent for permeabilizing the membrane, capable of transporting said nucleic acid across the cytoplasmic or endosomal membranes of said eukaryotic cell.

9. The composition as claimed in claim 5, wherein said polycationic phosphorus-containing dendrimer is associated noncovalently with said nucleic acid.

\* \* \* \* \*